US00PP22312P2

(12) United States Plant Patent
van Kleinwee

(10) Patent No.: US PP22,312 P2
(45) Date of Patent: Dec. 6, 2011

(54) *CALIBRACHOA* PLANT NAMED 'CALPRIBUL'

(50) Latin Name: ***Calibrachoa* spp.**
Varietal Denomination: Calpribul

(75) Inventor: Theodorus Cornelis van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/806,228

(22) Filed: Aug. 6, 2010

(51) Int. Cl.
*A01H 5/00* (2006.01)

(52) U.S. Cl. ..... Plt./413

(58) Field of Classification Search ..... Plt./413
See application file for complete search history.

*Primary Examiner* — Susan McCormick Ewoldt

(74) *Attorney, Agent, or Firm* — S. Matthew Edwards

(57) ABSTRACT

A new *Calibrachoa* plant named 'Calpribul' particularly distinguished by the relatively large sized, violet colored flowers, medium green foliage and compact plant habit with good branching

1 Drawing Sheet

Latin name of the genus and species of the plant claimed: *Calibrachoa* spp.

Varietal denomination: 'Calpribul'.

BACKGROUND OF THE NEW PLANT

The present invention comprises a new *Calibrachoa*, botanically known as *Calibrachoa* spp., and hereinafter referred to by the variety name 'Calpribul'.

'Calpribul' is a product of a planned breeding program. The new cultivar has relatively large sized, violet colored flowers, medium green foliage and compact plant habit with good branching.

'Calpribul' originated from a hybridization made in May 2005 in a controlled breeding environment in Enkhuizen, Netherlands. The female parent was the unpatented proprietary plant designated 'GO332-1' with light blue flowers, few branches, and is later to flower.

The male parent of 'Calpribul' was an unpatented proprietary plant identified as 'D4809-1' with dark violet blue flowers, less vigor, and a smaller flower. The resultant seed was sown in February 2006.

'Calpribul' was selected as one flowering plant within the progeny of the stated cross in May 2006 in a controlled environment in Enkhuizen, Netherlands.

The first act of asexual reproduction of 'Calpribul' was accomplished when vegetative cuttings were propagated from the initial selection in May 2006 in a controlled environment in Enkhuizen, Netherlands.

BRIEF SUMMARY OF INVENTION

Horticultural examination of plants grown from cuttings of the plant initiated in May 2006, and continuing thereafter, has demonstrated that the combination of characteristics as herein disclosed for 'Calpribul' are firmly fixed and are retained through successive generations of asexual reproduction.

'Calpribul' has not been observed under all possible environmental conditions. The phenotype may vary significantly with variations in environment such as temperature, light intensity and day length.

Plant Breeder's Rights for this cultivar were applied for in Canada on Feb. 9, 2010 (#10-6821) and in CVPO on Sep. 29, 2009 (#2009/1908). 'Calpribul' has not been made publicly available more than one year prior to the filing of this application.

The following traits have been repeatedly observed and are determined to be basic characteristics of the new variety. The combination of these characteristics distinguishes this *Calibrachoa* as a new and distinct variety.

BRIEF DESCRIPTION OF THE PHOTOGRAPHS

The accompanying photographic drawing shows typical flower and foliage characteristics of 'Calpribul' with colors being as true as possible with an illustration of this type. The photographic drawing shows a flowering potted plant of the new variety and a close-up of the flowers.

DETAILED BOTANICAL DESCRIPTION

The aforementioned photographs were taken in April 2010 from plants growing in a greenhouse trial in Gilroy, Calif. USA. These plants were growing in 4 inch pots and were approximately 15-16 weeks of age.

The plant descriptions and measurements were taken in mid May 2010 in Hillscheid, Germany on 9 week old plants that were growing in 12 cm pots and were grown without pinching, on benches in a greenhouse at a minimum temperature (heating temperature) of 12° C.

Color references are made to The Royal Horticultural Society Colour Chart (R.H.S.) 2001.

TABLE 1

DIFFERENCES BETWEEN THE NEW VARIETY 'CALPRIBUL' AND A SIMILAR VARIETY

| | 'Calpribul' | 'Cal Litbule'(U.S. Plant Pat. No. 19,244) |
|---|---|---|
| Flower color: | RHS N87A | RHS N82B |
| Corolla tube length: | Longer | Shorter |

TABLE 1-continued

DIFFERENCES BETWEEN THE NEW VARIETY 'CALPRIBUL' AND A SIMILAR VARIETY

| | 'Calpribul' | 'Cal Litbule'(U.S. Plant Pat. No. 19,244) |
|---|---|---|
| Pedicel length: | Longer | Shorter |
| Leaf length: | Longer | Shorter |
| Sepal length: | Longer | Shorter |

Plant:

*Form, growth and habit.*—Initially low and semi-mounding, then more trailing, good branching, pinching enhances the number of branches.

*Plant height.*—8-12 cm.

*Plant height (inflorescence included).*—10-11 cm.

*Plant width.*—26-32 cm.

Roots:

*Number of days to initiate and produce roots.*—18-24 days at about 22 degrees C.

*Type.*—Fine, fibrous, free branching.

*Color.*—RHS N158B.

Foliage:

*Arrangement.*—Alternate, simple.

*Immature, leaf color, upper surface.*—RHS 137B to RHS 137C.

*Lower surface.*—RHS 137C to RHS 137D.

*Mature, leaf color, upper surface.*—RHS 137A to RHS 137B.

*Lower surface.*—RHS 137C.

*Length.*—2.9-3.5 cm.

*Width.*—1.2-1.5 cm.

*Shape.*—Lanceolate to elliptical.

*Base shape.*—Acute.

*Apex shape.*—Acute to obtuse.

*Margin.*—Entire.

*Texture, upper surface.*—Densely covered with very short, fine hairs.

*Lower surface.*—Densely covered with very short, fine hairs.

*Color of veins, upper surface.*—RHS144A.

*Color of veins, lower surface.*—RHS 144A.

*Petiole color.*—RHS 144A.

*Length.*—RHS 144A.

*Diameter.*—0.1-0.2 cm.

*Texture.*—Densely covered with short hairs.

Stem:

*Quantity of main branches per plant.*—15-17.

*Color of stem.*—Closest to RHS 138B with small blotches of RHS 177B.

*Length of stem.*—11-15 cm.

*Diameter.*—0.15-0.2 cm.

*Length of internodes.*—0.5-1.3 cm.

*Texture.*—Hairs in various sizes; some glandular hairs.

*Color of pedicel.*—RHS 143C.

*Length of pedicel.*—2.2-2.6 cm.

*Diameter of pedicel.*—0.1 cm.

*Texture of pedicel.*—Dense pubescense.

Inflorescence:

*Type.*—Flowers solitary in upper leaf axis; flowers face mainly horizontally, mostly 5-fused lobes forming a funnel form flower. Continuous flowering throughout the Summer.

*Quantity of inflorescences per plant.*—Approximately 20-30.

*Lastingness of individual blooms on the plant.*—About 8-10 days.

*Fragrance.*—None.

Bud (just when opening/showing color):

*Color.*—RHS 79C to RHS 79D.

*Length.*—Up to 2.6 cm.

*Width.*—0.5-0.8 cm.

*Shape.*—Oblong.

Immature inflorescence:

*Flower horizontal diameter.*—2.9-3.5 cm.

*Color petals, upper surface.*—Closest to RHS 83B but a little brighter, with RHS 83A around the throat.

*Color petals, lower surface.*—A lighter hue than RHS 83D.

Mature inflorescence:

*Flower horizontal diameter.*—3.2-4.0 cm.

*Flower height (vertical).*—About 2.5 cm.

*Color petals, upper surface.*—RHS N87A with closest to RHS 83B around the throat.

*Lower surface.*—RHS N82C with RHS 146A mid veins.

*Apex shape.*—Truncate to slightly retuse.

*Margin.*—Entire.

*Waviness of petals.*—Slight.

*Petal lobation.*—Weak.

*Petal texture, upper surface.*—Papillose, glabrous.

*Lower surface.*—Short hair along the veins.

*Corolla tube color outside.*—RHS 1C with RHS N79A veins.

*Inside.*—RHS 3B to RHS 3C with blotches of RHS 1B to RHS 1C; fine weak veins of RHS 146B.

*Corolla tube length.*—1.8-2.0 cm.

*Corolla texture, outside.*—Hairs along the protruding veins.

*Inside.*—Papillose.

Sepals:

*Color, upper surface.*—RHS 137A.

*Lower surface.*—RHS 137C.

*Length.*—1.6-1.8 cm.

*Width.*—0.3-0.5 cm.

*Shape.*—Oblanceolate.

*Apex shape.*—Obtuse.

*Based.*—Fused.

*Margins.*—Entire.

*Texture, upper surface.*—Densely covered with very short hairs.

*Lower surface.*—Densely covered with very short hairs.

Reproductive organs:

*Pistil.*—1.

*Length.*—1.2 cm.

*Style color.*—RHS 145A.

*Style length.*—0.8-0.9 cm.

*Stigma color.*—RHS 143B.

*Stamens.*—5.

*Color of filaments.*—RHS 4D.

*Length filaments.*—0.5-1.0 cm.

*Color of pollen.*—RHS 13B.

Pollen amount.—Moderate.

*Fertility/seed set.*—Has not been observed on this hybrid.

Disease/pest resistance: Disease/pest resistance has not been observed on this hybrid.

What is claimed is:

1. A new and distinct variety of *Calibrachoa* plant named 'Calpribul' substantially as illustrated and described herein.

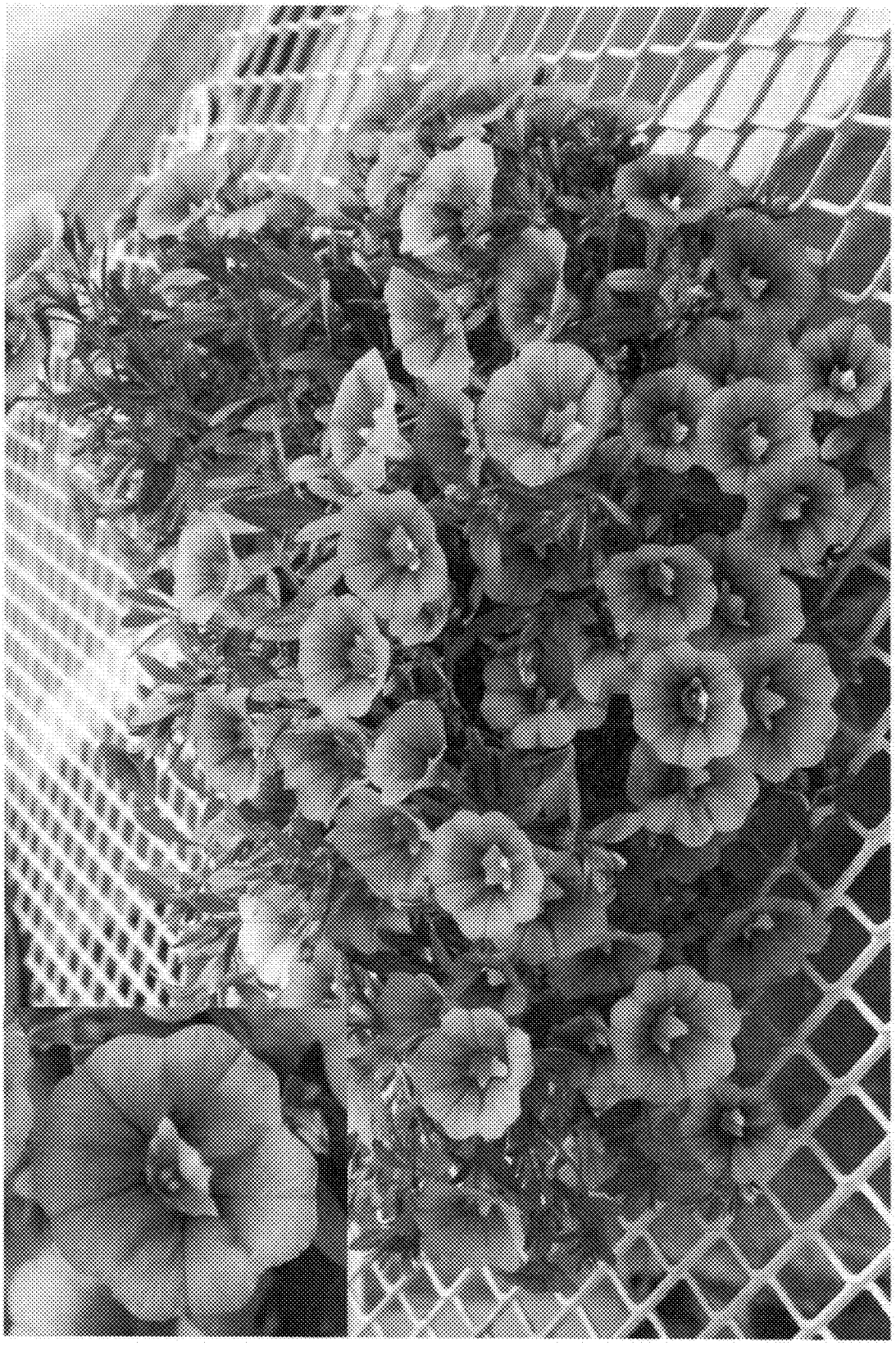

* * * * *